United States Patent [19]

Long

[11] 4,288,598
[45] Sep. 8, 1981

[54] PYRIDINE-2,3,6-TRIONES

[75] Inventor: William E. Long, Brentwood, England

[73] Assignee: Ciba-Geigy AG, Basel, Switzerland

[21] Appl. No.: 123,867

[22] Filed: Feb. 22, 1980

[30] Foreign Application Priority Data

Mar. 26, 1979 [GB] United Kingdom .............. 10539/79

[51] Int. Cl.³ .................... C07D 213/56; C07D 213/57
[52] U.S. Cl. ..................................... 546/288; 546/291; 430/392
[58] Field of Search ................................ 546/288, 291

[56] References Cited

U.S. PATENT DOCUMENTS 4,182,886 1/1980 Kitzing et al. ....................... 546/304

FOREIGN PATENT DOCUMENTS 2600675 7/1976 Fed. Rep. of Germany ...... 546/291

OTHER PUBLICATIONS

March, Advanced Organic Chemistry, Second Edition, p. 247, McGraw-Hill Pub., (1979).

Klingsberg, Pyridine and Its Derivatives, Part Three, pp. 595–596, Interscience Pub. (1962).
Klingsberg, Pyridine and Its Derivatives, Part Two, p. 482, Interscience Pub., (1961).

Primary Examiner—Alan L. Rotman
Attorney, Agent, or Firm—Sprung, Felfe, Horn, Lynch & Kramer

[57] ABSTRACT

New silver dye-bleach catalysts and the process for their manufacture are provided. These compounds have the general formula

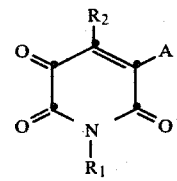

wherein A is an electron-withdrawing group and $R_1$ and $R_2$ are hydrogen, optionally substituted alkyl or optionally substituted aryl.

5 Claims, No Drawings

PYRIDINE-2,3,6-TRIONES

This invention relates to novel pyridine-triones compounds, to their production and to their use as silver dye-bleach catalysts in photographic processes.

According to the present invention these are provided compounds of the general formula

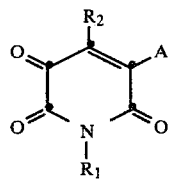
(1)

wherein A is an electron-withdrawing group, and $R_1$ and $R_2$ are hydrogen, optionally substituted alkyl or optionally substituted aryl.

Examples of suitable groups A are cyano and carboxamide. Alkyls for $R_1$ and $R_2$ contain 1 to 6, preferably 1 to 4 carbon atoms. Aryl represents mono- or bicyclic, saturated or aromatic ring systems, preferably phenyl. Substituents of these alkyl groups are alkoxy with 1 to 4 carbon atoms, hydroxy or halogen, such as fluorine, chlorine or bromine. The aryl (phenyl) groups may be substituted by the same substituents and further by alkyl of 1 to 4 carbon atoms.

Examples of compounds of formula (1) are compounds of formulae

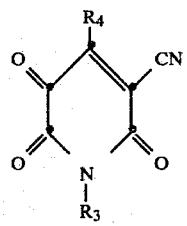
(2)

and

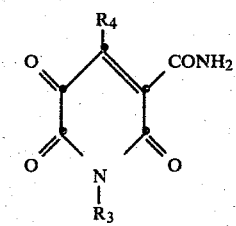
(3)

wherein $R_3$ and $R_4$ are each alkyl of 1 to 4 carbon atoms.

A particularly useful compound of formula (2) is the compound of formula

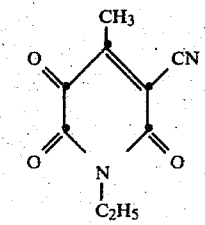
(4)

and the compound of formula

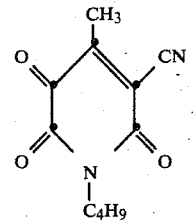
(5)

A particularly useful compound of formula (3) is the compound of formula

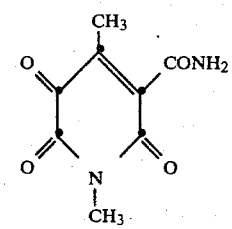
(6)

Compounds of formula (1) may be prepared by hydrolysis using aqueous acid of an azomethine compound of formula

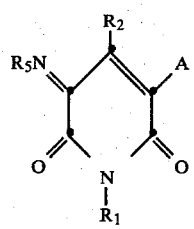
(7)

wherein A, $R_1$ and $R_2$ have the meanings assigned to them above and $R_5$ comprises an optionally substituted aryl or an optionally substituted heterocyclic ring.

Preferably, $R_5N$ comprises an optionally substituted p-phenylene diamine residue.

Alternatively, compounds of formula (1) may be prepared from hydroxy-pyridones of formula

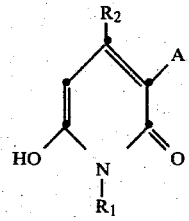
(8)

wherein A, $R_1$ and $R_2$ have the meanings assigned to them above, by reaction with a nitroso compound $R_5NO$, wherein $R_5$ has the meaning assigned to it above. Compounds of formula (7) are possible intermediates in this reaction.

The compounds of formula (1) are useful as silver dye-bleach catalysts in photographic processes. They are especially useful in a photographic process which involves contacting a preformed silver photographic image with a coating of a reducible dye such as an azomethine or triphenyl-methane dye, and processing with a solution of the compound of formula (1) together with an acid and a silver complexing agent, causing the compound of formula (1) to be reduced imagewise to an active dihydro form, which diffuses imagewise into the dye layer and bleaches it imagewise, leaving a dye image which is the negative of the original silver image.

Suitable dyes for the above process are azomethine or triphenylmethane dyes, including particularly those of formula (7) when $R_5N$ comprises a substituted paraphenylene diamine residue. Suitable silver complexing agents are chloride, bromide or iodide ions or thiourea.

EXAMPLE 1

5-Cyano-1-ethyl-4-methylpyridine-2,3,6-trione 1.02 g of 3-Cyano-1-ethyl-4-methyl-5-[4-(N-ethyl-N-hydroxyethylamino)phenylimino]-pyridine-2,6-dione (prepared as described in German Offenlegungsschrift No. 2808825) is stirred in 7 ml of water, and concentrated hydrochloric acid is slowly added until the blue dye had disappeared. A pale yellow solid precipitates, and is filtered off and recrystallised from ethyl acetate/petrol, yield 0.32 g, m.p. 159°–160° C. This is the compound of formula (4).

EXAMPLE 2

1,4-Dimethylpyridine-5-carboxamide-2,3,6-trione 0.91 g of 1,4-Dimethyl-6-hydroxypyrid-2-one-3-carboxamide and 0.75 g of N,N-dimethyl-4-nitrosoaniline are stirred in 20 ml of acetic acid for 1 hour, and then 10 ml of water and 10 ml of concentrated hydrochloric acid are added. A yellow solid slowly precipitates and is filtered off. Yield 0.43 g, m.p. 210°–215° C. (dec.). This is the compound of formula (6).

EXAMPLE 3

1-Butyl-5-cyano-4-methylpyridine-2,3,6-trione

Prepared using the method of Example 2, with 1.03 g of 1-butyl-3-cyano-6-hydroxy-4-methylpyrid-2-one and 0.76 g of dimethyl-nitrosoaniline. Recrystallised from petrol/ethyl acetate, yield 0.54 g, m.p. 134°–135° C. This is the compound of formula (5).

EXAMPLE 4

Bleaching of an azomethine dye.

An assembly is prepared which comprises a transparent cellulose triacetate film base 150 microns thick having coated thereon a layer which comprises 10 mg/dm² of compound of formula

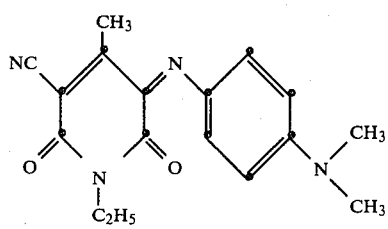
(101)

in 30 mg/dm² of gelatin.

A strip of this coated assembly and a strip of a silver image print of a bar chart ranging in frequency from 0.11 to 10 line pairs per mm are contacted face to face with a processing solution of the following composition:

| Compound of formula (4) | 10 mg |
| --- | --- |
| 2-ethoxy ethanol | 0.5 ml |
| added to hydrochloric acid (0.25N) | 100 ml. |

After a contact time of 1 minute, an image of the bar chart is produced in the dye coating, giving an 88% response at 10 lines/mm.

EXAMPLE 5

Bleaching of a triphenylmethane dye.

Similar strips are taken as in Example 4, but the dye rosaniline of formula

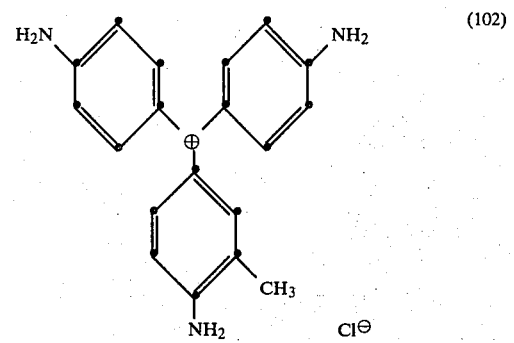
(102)

is used.

After 1 minute contact time a magenta image was seen in the dye layer.

I claim:

1. A compound of the general formula

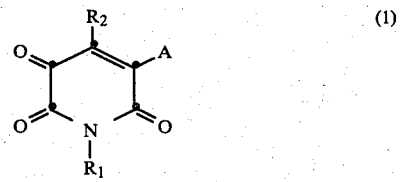
(1)

wherein A is cyano or carboxamide and $R_1$ and $R_2$ are hydrogen, alkyl of 1 to 6 carbon atoms or alkyl of 1 to 6 carbon atoms substituted by a substituent selected from the group consisting of hydroxy, halogen and alkoxy of 1 to 4 carbon atoms, phenyl or phenyl substituted by a substituent selected from the group consisting of hydroxy, halogen, alkyl of 1 to 4 carbon atoms and alkoxy of 1 to 4 carbon atoms.

2. A compound according to claim 1 of the formula

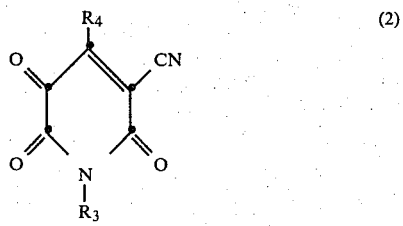
(2)

and

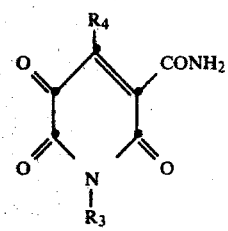
(3)
wherein $R_3$ and $R_4$ are each alkyl of 1 to 4 carbon atoms.
3. A compound according to claim 1 of the formula
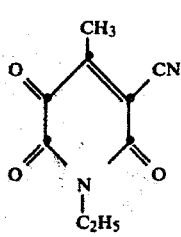
(4)
4. A compound according to claim 1 of the formula
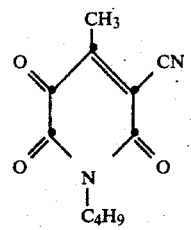
(5)
5. A compound according to claim 1 of the formula
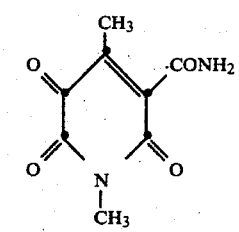
(6)
* * * * *